(12) United States Patent
Fritsch

(10) Patent No.: US 9,907,699 B2
(45) Date of Patent: Mar. 6, 2018

(54) ONE STEP TYMPANOSTOMY TUBE AND METHOD OF INSERTING SAME

(71) Applicant: Michael H Fritsch, Indianapolis, IN (US)

(72) Inventor: Michael H Fritsch, Indianapolis, IN (US)

(73) Assignee: Domestic Legacy Limited Partnership, Indianapolis, IN (US)

( * ) Notice: Subject to any disclaimer, the term of this patent is extended or adjusted under 35 U.S.C. 154(b) by 336 days.

(21) Appl. No.: 13/764,875

(22) Filed: Feb. 12, 2013

(65) Prior Publication Data

US 2014/0012282 A1   Jan. 9, 2014

Related U.S. Application Data

(60) Provisional application No. 61/668,407, filed on Jul. 5, 2012.

(51) Int. Cl.
   *A61F 11/00* (2006.01)

(52) U.S. Cl.
   CPC ............ *A61F 11/002* (2013.01); *A61F 11/00* (2013.01)

(58) Field of Classification Search
   CPC .............................. A61F 11/00; A61F 11/002
   USPC .............................................. 606/109; 623/10
   See application file for complete search history.

(56) References Cited

U.S. PATENT DOCUMENTS

| | | |
|---|---|---|
| 2,670,738 A | 3/1954 | Gibbons |
| 3,636,943 A * | 1/1972 | Balamuth .................... 601/2 |
| 3,807,409 A | 4/1974 | Paparella et al. |
| 3,897,786 A | 8/1975 | Garnett et al. |
| 4,695,275 A | 9/1987 | Bruce et al. |
| 5,053,040 A | 10/1991 | Goldsmith, III |

(Continued)

FOREIGN PATENT DOCUMENTS

| | | |
|---|---|---|
| EP | 0 445 946 B1 | 5/1994 |
| WO | WO2010045432 | 4/2010 |

OTHER PUBLICATIONS

PCT International Search Report dated Oct. 24, 2013 for Fritsch; International Application No. PCT/US13/50931.

*Primary Examiner* — Darwin Erezo
*Assistant Examiner* — Martin T Ton
(74) *Attorney, Agent, or Firm* — E. Victor Indiano; Indiano & McConnell, LLC

(57) ABSTRACT

A tympanostomy tube for insertion into and residence in a tympanic membrane of a mammal, is disclosed. The tympanostomy tube includes a body including a first end portion, a second end portion, a central portion dispensed between the first and second end portions. An axially extending passageway has a first open end disposed adjacent the first end portion, and a second open end disposed adjacent the second end portion, and an axis extending between the first open end and second open end. The first end portion includes a relatively enlarged diameter, generally radially extending flange. The central portion includes a reduced diameter portion sized for extending through and residing in tissue of the tympanic membrane. The second end portion includes a relatively enlarged diameter second flange disposed adjacent the second end portion. The second flange includes a perimetral edge having an incising portion sufficiently sharpened to cut as a knife through the tympanic membrane during insertion of the tympanostomy tube in the tympanic membrane.

11 Claims, 12 Drawing Sheets

(56) References Cited

U.S. PATENT DOCUMENTS

| | | |
|---|---|---|
| 5,137,523 A | 8/1992 | Peerless et al. |
| 5,178,623 A | 1/1993 | Cinberg |
| 5,207,685 A * | 5/1993 | Cinberg ............... A61F 11/002 606/1 |
| 5,254,120 A | 10/1993 | Cinberg et al. |
| 5,317,938 A * | 6/1994 | de Juan, Jr. ........... A61B 17/32 76/104.1 |
| 5,389,088 A | 2/1995 | Hageman |
| 5,443,493 A | 8/1995 | Byers et al. |
| 5,489,286 A | 2/1996 | Cinberg et al. |
| 5,643,280 A | 7/1997 | Del Rio et al. |
| 5,645,584 A | 7/1997 | Suyama |
| 5,775,336 A | 7/1998 | Morris |
| 5,827,295 A | 10/1998 | Del Rio et al. |
| 6,042,574 A | 3/2000 | O'Halloran |
| 6,045,528 A | 4/2000 | Arenberg et al. |
| 6,120,484 A | 9/2000 | Silverstein |
| 6,245,077 B1 | 6/2001 | East et al. |
| 6,361,526 B1 | 3/2002 | Reisdorf et al. |
| 6,379,323 B1 * | 4/2002 | Patterson ............. A61F 11/002 604/8 |
| 6,406,453 B1 | 6/2002 | Goode et al. |
| 6,648,873 B2 | 11/2003 | Arenberg et al. |
| 6,689,302 B2 | 2/2004 | Reisdorf et al. |
| 6,770,080 B2 | 8/2004 | Kaplan et al. |
| 6,936,023 B2 | 8/2005 | Goode et al. |
| 7,097,661 B2 * | 8/2006 | Perry ................... A61F 11/002 604/285 |
| 7,704,259 B2 | 4/2010 | Kaplan et al. |
| 8,197,433 B2 | 6/2012 | Cohen |
| 8,480,610 B1 | 7/2013 | Hill |
| 8,480,611 B1 | 7/2013 | Alshemari |
| 8,529,495 B1 | 9/2013 | Alshemari |
| 2003/0033016 A1 | 2/2003 | Dees, Jr. |
| 2006/0004368 A1 | 1/2006 | Zaleski et al. |
| 2008/0058831 A1 | 3/2008 | Fujiwara |
| 2008/0058832 A1 | 3/2008 | Fujiwara |
| 2008/0215148 A1 | 9/2008 | Lesinski et al. |
| 2009/0209972 A1 | 8/2009 | Loushin et al. |
| 2009/0299379 A1 | 12/2009 | Katz et al. |
| 2010/0191331 A1 | 7/2010 | Steinhardt et al. |
| 2013/0060278 A1 | 3/2013 | Bozung et al. |

* cited by examiner

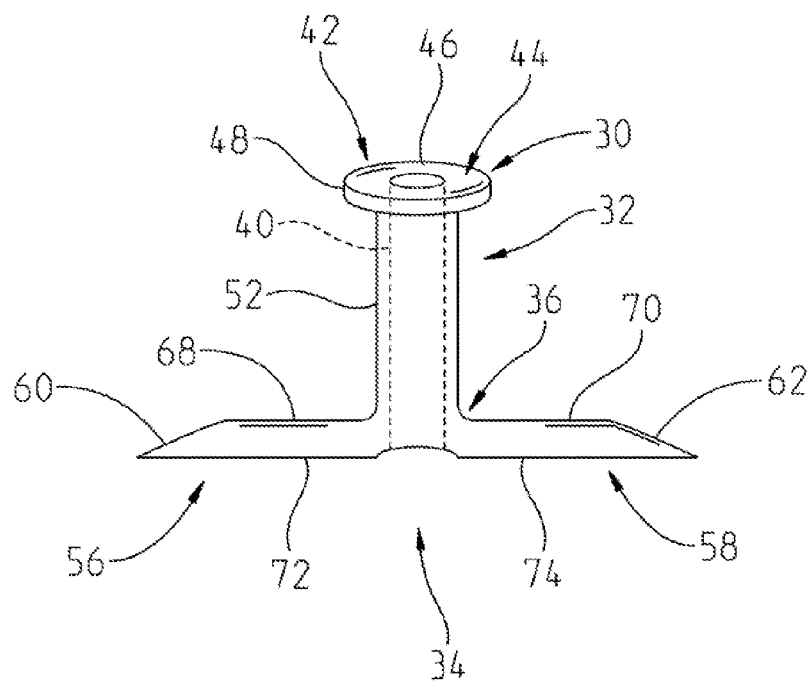
Fig. 3
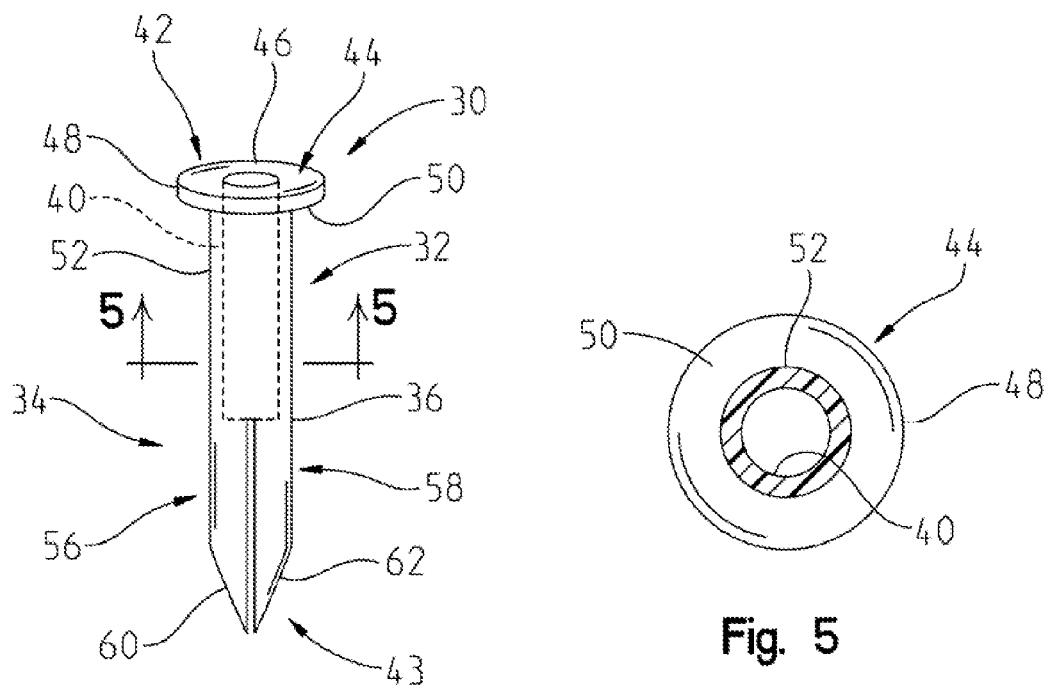
Fig. 4
Fig. 5

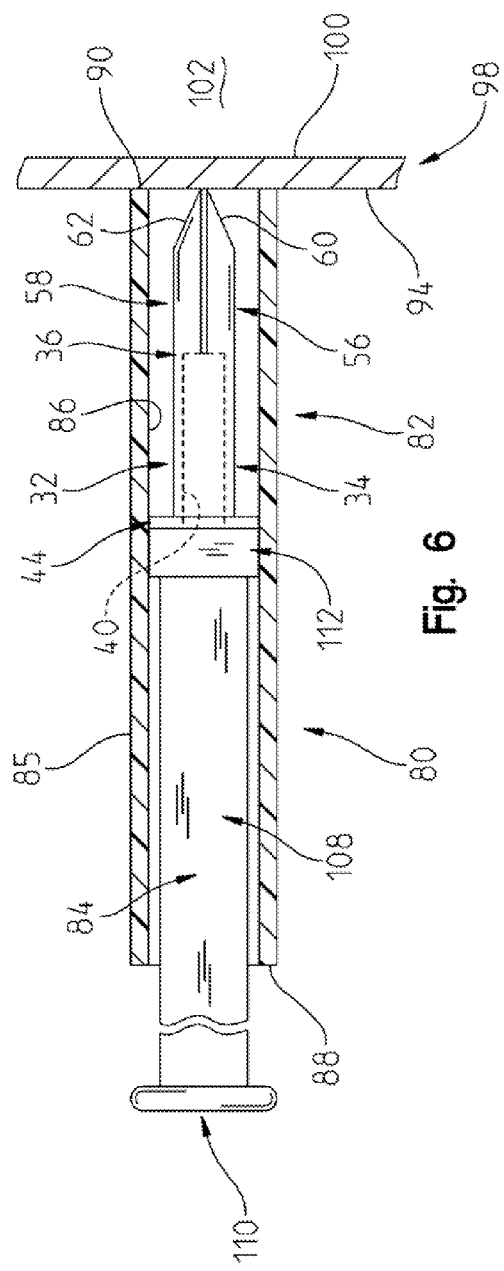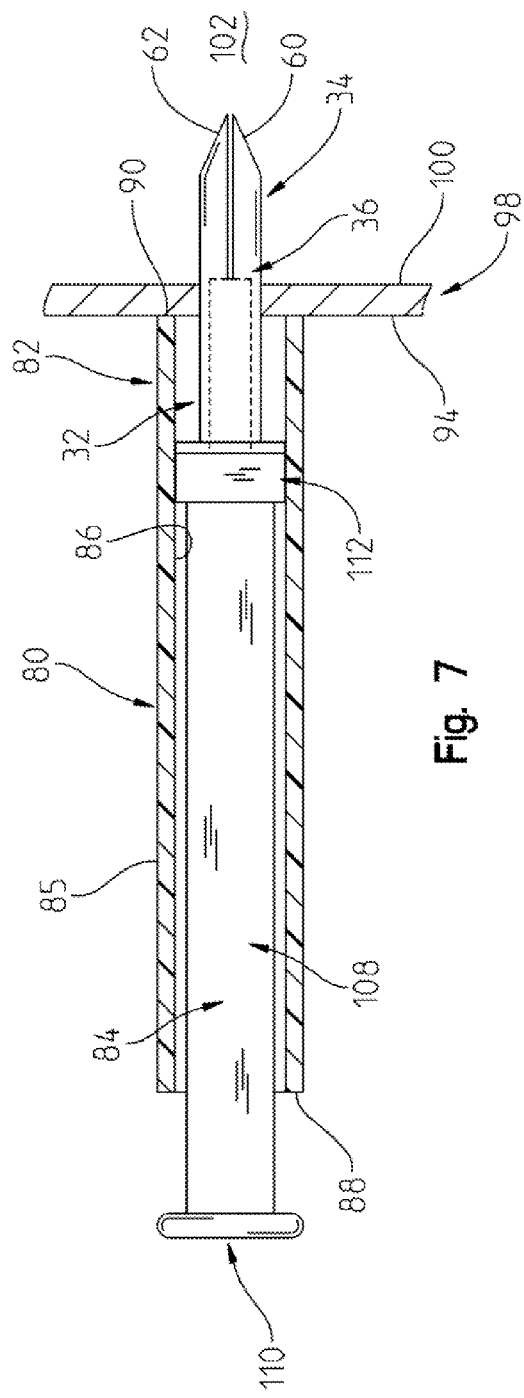

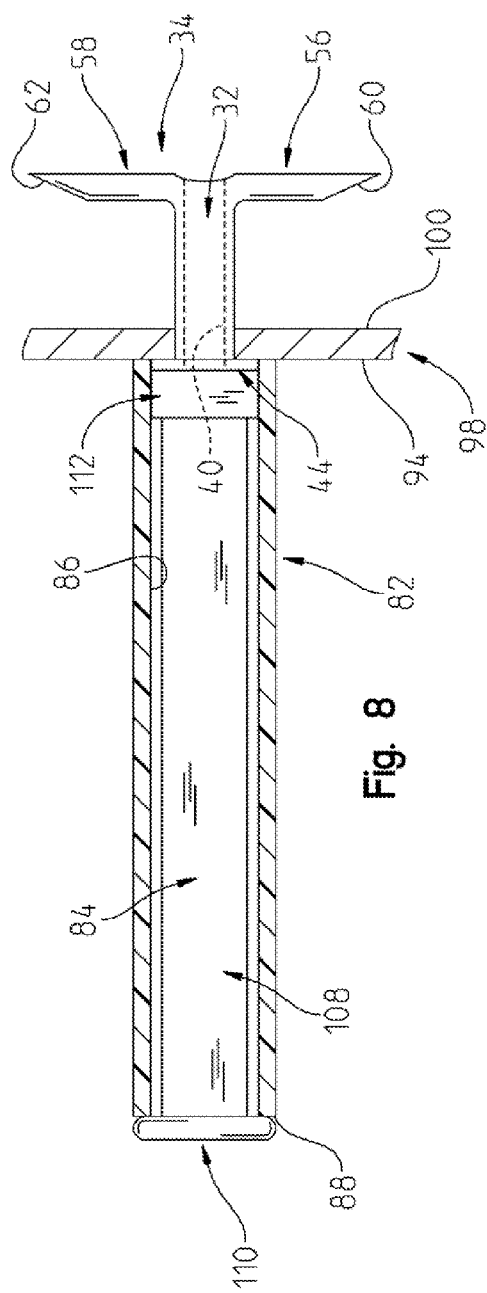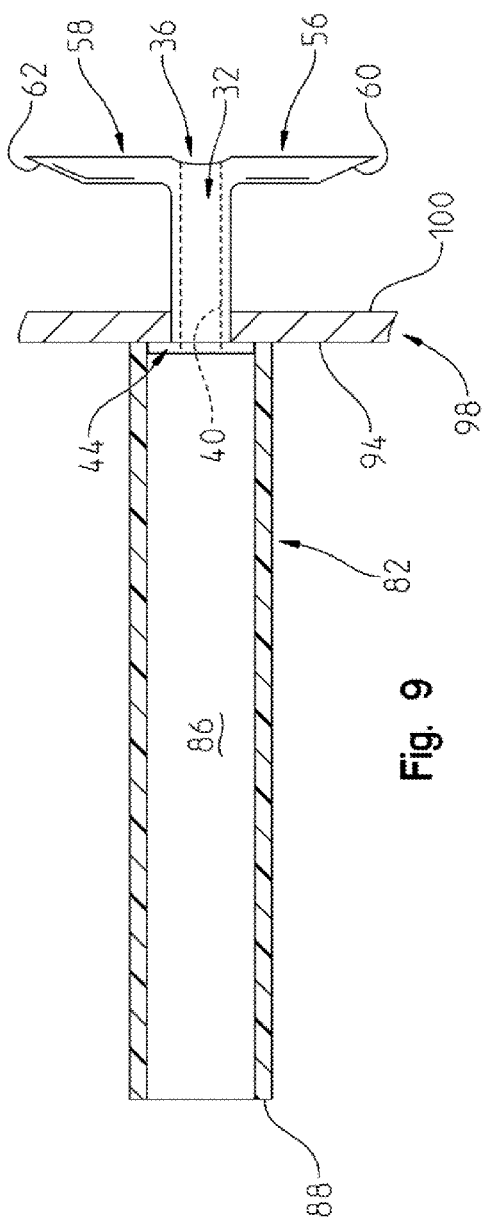

US 9,907,699 B2

ONE STEP TYMPANOSTOMY TUBE AND METHOD OF INSERTING SAME

PRIORITY STATEMENT

The present invention claims benefit of priority to Fritsch, U.S. provisional patent application No. 61/668,407, that was filed on 5 Jul. 2012 and is fully incorporated herein by reference.

I. TECHNICAL FIELD OF THE INVENTION

The present invention relates to medical devices, and more particularly, to a tympanostomy tube device used in connection with the insertion of a tympanastomy tube into a patient, and methods for inserting a tympanostomy tube in a patient.

II. BACKGROUND

From time to time, most younger children suffer from earaches. In many cases, an earache is caused by a build up of fluid in the middle ear that leads to an infection in the ear. Usually, the earache can be treated by giving the child an antibiotic that will help to treat this middle ear infection.

Unfortunately, antibiotics do not work well with all patients, for although the antibiotic helps to cure the infection, some patients accumulate fluid frequently enough within their middle ears so that it is necessary to take steps to aerate the middle ear to thereby help prevent the accumulation of fluid. This aeration helps to reduce the fluid and likelihood that bacteria will cause an infection in the accumulated fluid, and helps to reduce or eliminate the recurrence of earaches.

To treat such patients, a tympanostomy tube is often inserted into the eardrum to extend through the eardrum in order to keep the middle ear aerated for a prolonged period of time, and to prevent the accumulation of fluid in the inner ear. A tympanostomy tube is also know as a grommet, ear tube, pressure equalization tube, PE tube, or a myringotomy tube.

The operation to insert the tube involves a myringotomy and is performed under local or general anesthesia. A myringotomy is a surgical procedure in which a tiny incision is created in the eardrum, so as to relieve pressure caused by the excessive build up of fluid, or to drain puss, wherein a tube is inserted in the eardrum for residence over an extended period of time.

The most commonly used type of ear tube is shaped like a grommet. If a medical practitioner decides that the ear needs to be kept open and ventilated for a long period of time, a "T" shaped tube may be used, as these "T" tubes can stay in place two to four years or so. The materials of choice for creating such tubes are plastic materials such as silicone or teflon. Formerly, stainless steel tubes and other materials were popular, but are no longer used frequently.

The placement of ear tubes in a child's ear is a very common procedure. In the U.S., it is estimated that the most common reason for a child to undergo a general anesthetic is the insertion of such ear tubes within the child's ear. Ear tubes (tympanostomy tubes) generally remain within the eardrum for an extended period of time, usually lasting between six months and two years, although "T" tubes can last for four years or longer. Ear tubes generally spontaneously fall out of the eardrum as the skin of the eardrum slowly migrates out toward the ear canal wall over time. The ear drum usually closes without a residual hole at the tube site, but in a small number of cases, a perforation can exist.

In the conventional manner for performing tube insertion, first a myringotomy incision is made by inserting a needle-like knife into the ear canal to make the incision. Secondly, after the incision is made, the grommet-shaped ear tube is grasped with forceps and half of the grommet is inserted through the incision to finally rest suspended within the eardrum, so that the passageway in the grommet creates an air passage between the auditory canal and tympanic cavity.

A typical ear tube grommet is shaped similarly to a thread spool or wire spool. The grommet generally includes a reduced diameter central portion having a cylindrical radially outwardly facing surface. A first relatively enlarged diameter flange having a cylindrical radially outwardly facing perimetral edge is placed at one end of the reduced diameter portion, and a second, similarly configured enlarged diameter portion is placed at the second end of the reduced diameter portion. An axially extending passageway extends between a first end and a second end of the spool, which also includes generally planar upper and lower surfaces that have a generally round shape.

When inserted in the eardrum, the first enlarged diameter portion is disposed externally of the eardrum, with the second enlarged diameter portion disposed interiorly of the eardrum. The reduced diameter central portion extends through the eardrum. The result is that the first and second enlarged diameter portions prevent the grommet-shaped tube from becoming disconnected from the eardrum, to thus hold the grommet suspended within its position within the eardrum. When held in the proper position, the axially extending passageway of the tube can pass between the inner and outer surfaces of the eardrum, to thereby provide aeration to the middle ear, which comprises that portion of the ear that is disposed just interiorly of the eardrum.

Although such ear tubes and insertion devices serve their intended purposes, room for improvement exists. In particular, the generally small size of an ear tube makes it very difficult and tricky to manipulate the tube properly to insert it into the eardrum. In particular, it is difficult for even skilled surgeons to line up the grommet properly to insert it into the very tiny incision that was recently made in the eardrum by the knife. In essence, the doctor must move the knife into and out of the ear to make the incision, and then follow it up with an insertion of the grommet into the ear, within the same incision that was just made by the knife.

It is therefore one object of the present invention to provide an ear tube and insertion device that provides the potential to provide a more smooth and easy ear tube insertion procedure than that known currently by the applicant.

III. SUMMARY OF THE INVENTION

In accordance with the present invention, a tympanostomy tube for insertion into and residence in a tympanic membrane of a mammal is provided. The tympanostomy tube comprises a body including a first end portion, a second end portion, and a central portion disposed between the first and second end portions. An axially extending passageway has a first open end disposed adjacent the first end portion, and a second open end disposed adjacent the second end portion, and an axis extending between the first open end and second open end. The first end portion includes a relatively enlarged diameter, generally radially extending flange. The central portion includes a reduced diameter portion sized for extending through and residing in tissue of the tympanic membrane. The second end portion includes a relatively enlarged diameter second flange disposed adjacent the second end portion. The second flange includes a perimetral edge having an incising portion sufficiently sharpened to cut through the tympanic membrane during insertion of the tympanostomy tube in the tympanic membrane.

The distal flange portion is eccentrically coupled to the shaft portion, so as to include a relatively elongated portion and a relatively shortened portion. The elongated portion and relatively shortened portion are disposed on generally opposite sides of the shaft portion. The relatively elongated portion includes a knife-like edge surface that is configured to be capable of cutting an incision into an eardrum, to facilitate insertion of the tympanostomy tube in an eardrum. Preferably, the distal flange is disposed at an oblique angle of between about 110 and 150 degrees relative to the axis of the shaft portion, to better position the cutting edge of the elongated portion of the distal shaft portion to cut through an eardrum.

To insert the alternate embodiment tympanostomy tube within an eardrum, the tube is first grasped with an appropriate instrument, such as forceps. The forceps are then employed to place the cutting edge of the tympanostomy tube adjacent to and in contact with an eardrum. The tympanostomy tube is pushed medially with the forceps to cause the knife-like radially outward edge of the distal flange to slice through the eardrum. The tympanostomy tube continues to be moved medially, to a point wherein the distal flange is disposed in the middle ear medially of the ear drum, the shaft portion extends through the eardrum, and the proximal flange is disposed externally of the eardrum. Preferably, the proximally-facing surface of the distal flange is positioned to rest against the medial (interior) surface of the eardrum, to thereby anchor the tympanostomy tube in its position, to help prevent the tympanostomy tube from being removed from the eardrum prematurely.

One feature of the present invention is that it includes a distal flange having a cutting edge, for cutting an incision in to the eardrum. The cutting edge may have micro-serrations in order to better cut into the eardrum tissue without tearing or rupturing the eardrum. This feature has the advantage of enabling the tube itself to make the incision, to thereby make the placement of a tympanostomy tube in an eardrum more easily accomplished.

Also in accordance with the present invention, an alternate "T" tube embodiment of tympanostomy tube system is disclosed. The tympanostomy tube includes a tympanostomy tube and an insertion device. The insertion device includes a generally cylindrical member having an axially-extending interior passageway that is sized for receiving a tympanostomy tube. The insertion device has an outer diameter generally small enough to enable the medical practitioner to insert the insertion device into an ear canal to a point wherein a distal end of the insertion device can engage an exteriorly disposed surface of an eardrum.

The alternate "T" tympanostomy tube includes a proximal portion and a distal portion. The proximal portion is generally tubular in nature, and includes an axially-extending interior passageway. The proximal portion has an exterior diameter sized for being received within the interior axially-extending passageway of the insertion device.

The tympanostomy tube also includes a distal portion having at least a first leg and a second leg. Each of the first and second legs include a proximal end that couples the particular leg to the distal end of the proximal portion of the tympanostomy tube, and a distal end. The distal ends of the respective at least first and second distally disposed legs are configured to comprise cutting surfaces capable of incising the eardrum to permit the tympanostomy tube to be passed at least partially through the eardrum. The distal legs of the tympanostomy tube are movable between an insertion position wherein the first and second legs are disposed generally coaxially with the proximal portion, and a maintenance position, wherein the first and second legs are disposed at an oblique angle to the proximal portion of the tube.

The at least first and second distal legs can be placed in their insertion position against the eardrum. Then, the distal tip of the first and second distal legs can be employed to pierce and incise the eardrum. This allows the distal legs to be passed through the eardrum to a point wherein the first and second distal legs are disposed generally interiorly of the eardrum and within the tympanic cavity without needing a prior incision and knife blade. When the tympanostomy tube is inserted in the eardrum, a portion of the proximal portion of the tympanostomy tube extends through the eardrum, and the proximal end of the proximal portion is positioned generally exteriorly of the eardrum. When so positioned, the distal legs of the tympanostomy tube move from their insertion position to their maintenance position to help anchor the tube to the eardrum, to prevent the tube from being removed from the ear.

Preferably, the first and second legs are formed to be biased to normally move from their insertion position to their maintenance position. Additionally, the distal legs should be formed from a plastic having a memory so that when in the maintenance position, the distal legs extend along a line generally perpendicular to the axis of the central passageway of the proximal portion of the tympanostomy tube.

One feature of the alternate embodiment tympanostomy tube includes distal legs having surfaces that are configured to serve and operate as a knife for incising the eardrum. This feature has the advantage of simplifying the incision process, as it converts what was formerly a two-step process into a single step process. As discussed above, the prior art generally employs a knife to make an incision into the eardrum in the first step. The second step in the prior art is to then insert the grommet into the incision just made, after the knife is withdrawn from the ear canal.

In the alternate "T" tube embodiment, the insertion tube is preferably placed against the exterior surface out of the eardrum. The tympanostomy tube has been inserted into the central passageway of the insertion device, with the distal legs placed in their insertion position, such that they are disposed generally coaxially with the proximal portion. The knife-like distal edge of the legs is then used as a knife to create an incision in the eardrum.

By continuously pushing the tympanostomy tube in an axial direction, such as through the action of a piston or plunger, the distal legs can be moved through the eardrum, to a point wherein the distal legs are disposed fully within the middle ear portion of the ear (tympanic cavity). The outward biasing of the distal legs then causes the distal legs to move from an insertion position wherein they are axially aligned with the proximal portion, to a maintenance position wherein they are preferably almost fully perpendicular to the axis of the proximal portion and forming a generally "T" shape. When the distal legs are disposed at this generally perpendicular maintenance position, the distal legs can engage the interior surface of the eardrum, to thereby make the tube resistant to removal or extrusion from the ear, or becoming dislodged from the eardrum.

In accordance with a further embodiment of the present invention, a method is provided for inserting a tympanastomy tube into a tympanic membrane for continued residence in a tympanic membrane having an interiorly facing surface in the tympanic cavity and an exteriorly facing surface in the auditory canal. The method comprises providing a tympanostomy tube comprising a body including a first end portion, a second end portion, a central portion disposed between the first and second end portions, and an axially extending passageway having a first open end disposed adjacent the first end portion, a second open end disposed adjacent the second end portion, and an axis extending between the first open end and second open end. The first end portion includes a relatively enlarged diameter, generally radially extending flange. The central portion includes a reduced diameter portion sized for extending through and residing in tissue of the tympanic membrane, and the second end portion includes a relatively enlarged diameter second flange disposed adjacent the second end portion.

The first end is intended to remain disposed exteriorly of the drum while the second end is disposed interiorly of the drum. The second flange includes a perimetral edge having a sharp incising portion for cutting through the tympanic membrane during insertion of the tympanostomy tube in the tympanic membrane. A forceps is provided having first and second opposed blades operable to grasp an object. The forceps are used to grasp the tympanostomy tube wherein the first blade is disposed in the axially extending cavity and the second blade is disposed exteriorly of the central portion. The forceps are used to position the sharp incising portion of the second flange at an oblique angle to the exteriorly facing surface of the tympanic membrane. The tympanostomy tube is urged in a medial direction to cause the sharp incising portion to engage the tympanic membrane and to cut through the tympanic membrane. The tympanostomy tube is positioned in the tympanic membrane so that the tympanostomy tube resides in the tympanic membrane with the passageway operable to conduct air between the tympanic cavity and the auditory canal.

These other features of the present invention will become apparent to those skilled in the art upon a review of the detail of the drawings appended hereto, and the detailed description of the drawings presented hereunder.

IV. BRIEF DESCRIPTION OF THE DRAWINGS

FIG. 3 is a side view of the "T" type tympanostomy tube of the present invention, shown in its maintenance position;

FIG. 4 is a side view of the inventive tympanostomy tube of FIG. 3, shown in its insertion position;

FIG. 5 is a sectional view taken along the lines of 5-5 of FIG. 4;

FIG. 6 is a side, partly sectional view of the "T" type tympanostomy tube and insertion tools inserted in an ear canal, and just prior to the insertion of the tympanostomy tube in the tympanic membrane (eardrum);

FIG. 7 is a side, partly sectional, progressive view, showing the tympanostomy tube as it is being inserted into and extending through the tympanic membrane;

FIG. 8 is a side view of the "T" type tympanostomy tube and insertion tool of the present invention, showing the tympanostomy tube fully inserted into the tympanic membrane with the tympanostomy tube shown in its maintenance position;

FIG. 9 is a side, partly sectional view showing the tympanostomy tube fully inserted into the eardrum and in the maintenance position, with the plunger being removed from the insertion tube;

V. DETAILED DESCRIPTION OF INVENTION

Figure 21:
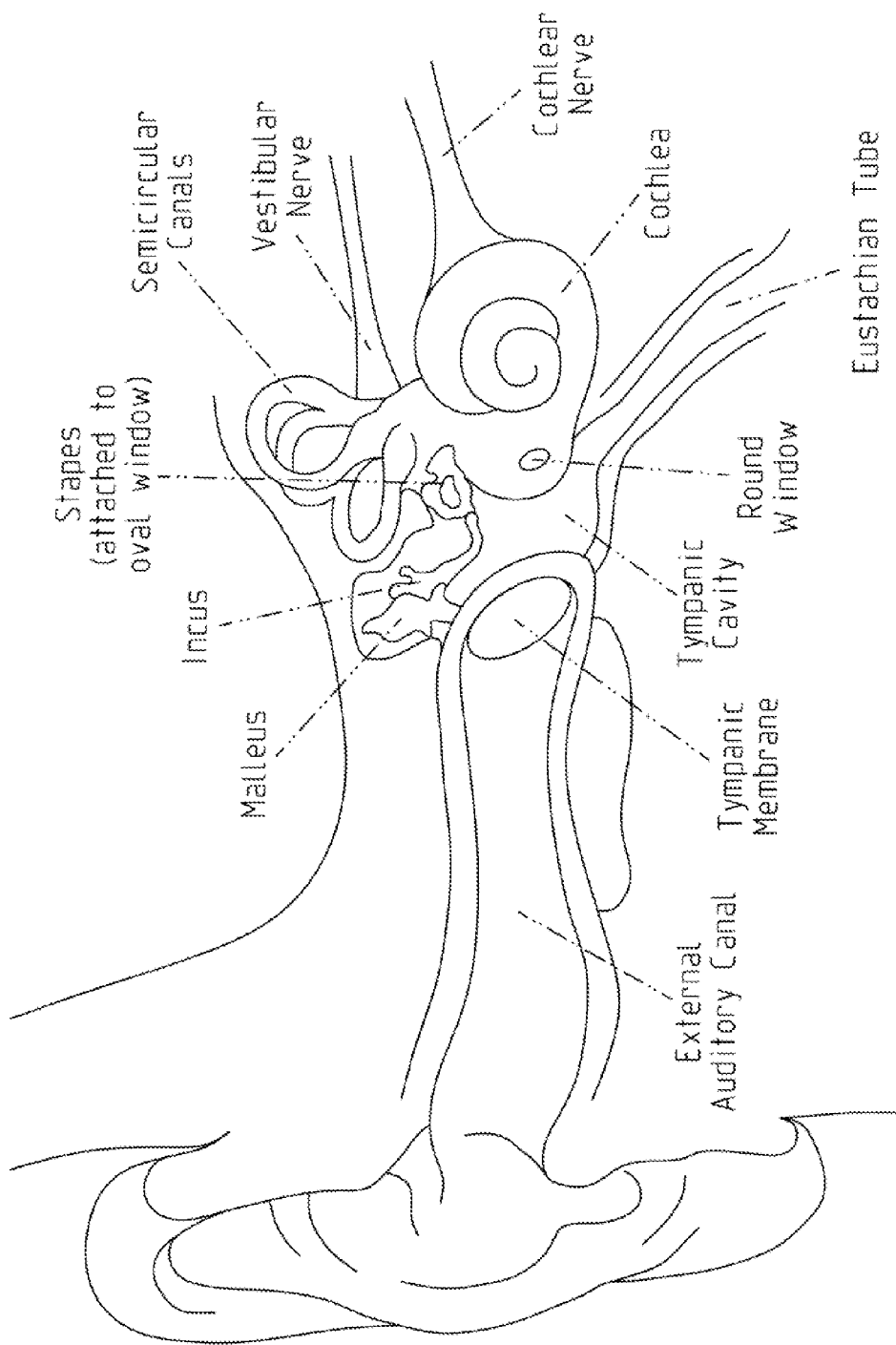
FIG. 21 is a diagrammatic view of the anatomy of the ear of a human being.

Turning first to FIG. 21, diagrammatic representation of the ear and its component parts is shown. This drawing is provided for reference to help provide context for the description of the tympanic tube of the present invention, and its placement within the ear.

The tympanic tube is inserted through the external auditory canal. The tube is positioned adjacent to the lateral (exterior) surface of the tympanic membrane, and then pushed through the tympanic membrane into the tympanic cavity. The tympanic cavity is also known as the middle ear. When fully inserted and resident in the tympanic membrane, the tympanic tube will include a distal portion that is disposed adjacent to the medial (interior) surface of the tympanic membrane, and a proximal end that will be disposed adjacent to the exterior surface of the tympanic membrane, and reside in the external auditory canal.

The tympanostomy tube also includes a generally cylindrical central portion that extends through the tympanic membrane, to couple the distal and proximal ends of the tympanic ends of the tympanostomy tube. When so inserted, the tympanostomy tube of the present invention provides for aeration of the middle ear by providing a venting passageway between the external auditory canal and the tympanic cavity. This aeration helps to reduce the amount of fluid buildup in the tympanic cavity, which thereby helps to reduce the likelihood of an infection occurring in the tympanic cavity. As infections in the middle ear often result in earaches to the patient, reducing the severity and/or number of middle ear infections leads to a reduction in ear aches for the patient.

Figure 1:
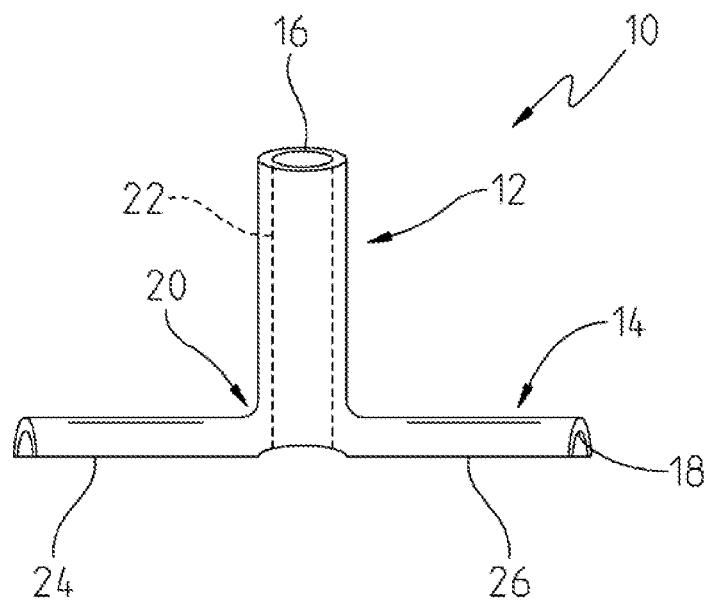
FIG. 1 is a side, partly schematic view of a prior art "T" type tympanostomy tube in its maintenance position.
Figure 2:
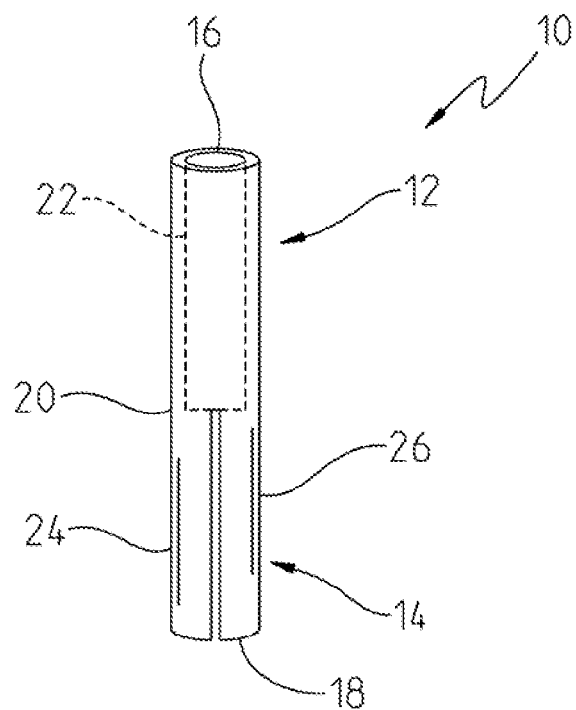
FIG. 2 is a side view of the prior art "T" type tympanostomy tube of FIG. 1 in its insertion position.

A prior known tympanostomy tube is shown in FIGS. 1 and 2. The prior tympanostomy tube 10 includes a proximal portion 12, and a distal portion 14. The tube 10 also includes a proximal end 16 that is located at the proximal end of the proximal portion 12, and a distal end 18 that is located at the distal end of the distal portion 14. A central portion 20 comprises the area of the tube 10 where the proximal portion joins the distal portion 18. An axially-extending passageway 22 extends through the proximal portion 12, and terminates at an open end in the central portion 20. When the tube 10 is in its insertion position, as shown in FIG. 2, the axially-extending passageway 22 extends all the way between the proximal end 16 and the distal end 18. The distal portion 14 includes a first axially extending distal leg member 24, and a second axially extending distal leg member 26.

When in the insertion position, as shown in FIG. 2, it will be noted that the first and second distal legs 24, 26 are disposed generally co-axially with the proximal portion 12, and that they have the same general dispositions and configurations as the proximal portion 12. However, the distal legs 24, 26 are moveable between an insertion position 14, as shown in FIG. 2, and a maintenance position as shown in FIG. 1. When in the maintenance position, the distal legs 24, 26 are disposed at generally an oblique angle, and preferably perpendicular to the axis of the axially-extending passageway 22 that extends through the proximal portion 12.

The insertion of the prior art tube 10 occurs by first employing a knife to make an incision in the tympanic membrane. The prior art tube 10 is then inserted through the freshly cut incision within the tympanic membrane to a point wherein the distal legs 24, 26 of the distal portion 14 are fully inserted into the tympanic cavity. As discussed above, this insertion procedure is a very tricky two-step procedure requiring the insertion and removal of the knife, that is followed by the insertion instrument that is used to grip and manipulate the tube, into the tympanic membrane. Once the tube 10 is successfully inserted, the instrument is removed from the ear canal.

A first embodiment "T" tympanostomy tube 30 of the present invention is shown in FIGS. 3-10. The tympanostomy tube 30 includes a proximal portion 32, a distal portion 34, and a central portion 36. The central portion 36 comprises that portion wherein the distal portion 34 joins the proximal portion 32.

An axially-extending passageway 40 extends axially through the proximal portion 32. When the tube 30 is in its insertion position, as shown in FIG. 4, the axially-extending passageway 40 also extends through the distal portion 34. The tube 30 also includes a proximal end 42 that is disposed at the proximal end of the proximal portion 32, and a distal end 43 that is disposed at the distal end of the distal portion 34.

A radially outwardly-extending flange 44 is formed at the proximal end 42 of the ear tube 30. The radially outwardly-extending flange includes a proximally-facing end surface 46, and a radially outwardly facing perimetral edge 48. An axially distally-facing surface 50 is disposed in an opposed relationship to the proximally-facing end surface 46.

The radially extending flange 44 is designed to have a diameter larger than the incision made by the tympanostomy tube 30. The purpose of this larger diameter is to ensure that the tympanostomy tube 30 remains in its appropriate place on the tympanic membrane after insertion. The relatively enlarged diameter flange 44 helps to ensure that the tympanostomy tube is not moved medially out of its engagement with the incision in the tympanic membrane, and through the tympanic membrane into the tympanic cavity.

The proximal portion 32 includes an axially-extending radially outwardly-facing generally cylindrical surface 52, which extends generally from the proximal end to the distal end of the proximal portion 32.

The distal portion 34 includes at least two distally disposed legs including a first distal leg 56 and a second distal leg 58. The first and second distal legs 56, 58 include, respectively first and second distal ends 60, 62. The first and second distal ends 60, 62 are beveled or otherwise configured to have knife like sharp edge surfaces, that comprise cutting surfaces. The first and second distal legs 60, 62 should have distal ends 60, 62 that are designed to be sharp enough to easily penetrate the tympanic membrane 98, upon the exertion of an axially and medially directed force on the tympanostomy tube 30, such as an axially-directed force that is applied to the proximally-facing surface 46 of the proximal flange 42 in a manner to move the tube 30 medially toward the tympanic cavity.

By employing cutting edge containing distal ends 60, 62, the need for using a knife to make a separate incision is thereby obviated. The insertion goes from two steps (i.e. (1) an incision followed by (2) the tube insertion, to one step (i.e. incise and insert, all in one). As best shown in FIGS. 3 and 4, the distal legs 56, 58 are moveable between an insertion position (FIG. 4) and a maintenance position (FIG. 3). In the insertion position (FIG. 4), the distal legs 56, 58 assume a position wherein they are disposed generally co-axially to the long axis of the passageway 40. In the insertion position, the cutting edges 60, 62 are positioned to cut into a membrane, such as the tympanic membrane, upon an axially, medially exerted force upon the tympanostomy tube 30.

From the insertion position (FIG. 4) the distal legs 56, 58 can be moved into a maintenance position as shown in FIG. 3. In the maintenance position, the long axes of each of the first and second distal legs 56, 58 are disposed at least at an oblique angle to the long axis of the passageway 40. Preferably, as shown in FIG. 3, the first and second legs 56, 58 are disposed generally co-axially to each other, and along an axis that is generally perpendicular to the long axis of the passageway 40.

When in the maintenance position as shown in FIG. 3, the distal legs 56, 58 each include laterally (exteriorly) facing surfaces 68, 70 and medially (interiorly) facing surfaces 72, 74. The designations "medial and lateral" are used to describe these surfaces because, when in the maintenance position and inserted into an ear, the laterally-facing surfaces 68, 70 face laterally, and are disposed against the medially-facing surface of the eardrum 98. The medially-facing surfaces 56, 58 face medially inwardly in the middle ear. It will be noted that the medially/lateral designations do not necessarily apply when a device is in the insertion position (FIG. 4) as in the insertion position, the laterally-facing surfaces 68, 70 become radially outwardly-facing surfaces, and the medially-facing surfaces 56, 58 become a radially inwardly-facing surfaces.

The method and process for inserting the tympanostomy tube 30 of the present invention is best described to with respect to FIG. 6-10.

In order to insert the tympanostomy tube 30 into an eardrum, an insertion tool set 80 is employed. The insertion tool set 80 includes a guide tube member 82, and a plunger or piston 84. The insertion tool tube member 82 is generally tube-like in configuration, and preferably has a cylindrical radially outwardly-facing exterior surface 85. A generally cylindrical radially inwardly-facing surface 86 defines an axially-extending interior passageway 87 (FIG. 9) which extends between the proximal end 88 and the distal end 90 and is open at both the proximal end 88 and the distal end 90. The passageway accommodates the interiorly positioned plunger 84.

The insertion tool 80 is sized and positioned so that it can be inserted into the external auditory canal, with the proximal end 88 being disposed exteriorly outwardly of the external auditory canal by a sufficient distance so they it can be grabbed and manipulated by the surgeon. The distal end 90, when the insertion tube 80 is fully inserted, should be placeable up against, and in contact with the laterally (exteriorly) facing surface 94 of the tympanic membrane 98.

The tympanic membrane 98 generally includes a laterally (exteriorly) facing surface 94, and a medially (interiorly) facing surface 100. The laterally facing surface 94 of the tympanic membrane 98 serves as the interior terminus of the external auditory canal, and the medial surface 100 serves as a wall of the tympanic cavity 102. Like a drumhead, the tympanic membrane 98 stretches across the external auditory canal.

A plunger member 84 is provided for axially moving the tympanostomy tube 30 in an axially medially direction down the insertion tube 80. The plunger 84 may comprise something as simple as a cylindrical rod. Alternately, the rod or plunger 84 may be formed as a plunger-type mechanism that is constructed similarly to a plunger of a syringe.

One preferred feature of the plunger 84 is that it be sized appropriately. In particular, the plunger should have a flange or head member 110 that has a diameter wider than the interior diameter of the insertion tube 80. This should be done so as to enable the plunger 84 to be inserted only to a certain depth in the insertion tube 80. Preferably, the length of the plunger 84 and the length of the tympanostomy tube 80 should be complementarily sized so that at full insertion of the plunger 84, the tympanostomy tube 30 has been moved axially in a direction and to a point where the tympanostomy tube 30 is appropriately seated within the tympanic membrane 98. The plunger 84 includes a cylindrical body portion 108, a proximal end 110 that includes enlarged diameter head 110, and a distal end 112.

Turning now to FIG. 6, the tympanostomy tube 30 and plunger 84 are shown in a position wherein the insertion tube 80 is inserted into the auditory canal, to a point wherein the distal end 90 of the insertion tube 80 rests against the lateral surface 94 of the tympanic membrane 98. The tympanostomy tube 30 is shown in its insertion position wherein the distal legs 56, 58 are disposed at a generally co-axially relationship with the axis of the axially-extending passageway 40.

The plunger has its distal end 112 disposed on and engaged with the upper surface of the radially outwardly extending flange 44 of the tympanostomy tube 200, with the proximal end 110 of the plunger 84 being disposed exteriorly of the insertion tube 80. FIGS. 6 and 7 do not show the length of the plunger 84 at full scale, due to space limitations. Had these space limitations not existed, the head 110 of the plunger would be shown as extending out further from the proximal end 88 of the insertion tube 80.

FIG. 7 is a progressive view that shows that the insertion procedure has progressed to the point wherein the plunger 84 has been moved axially medially, to push the tympanostomy tube 30 axially medially. This axially medial (distal) movement of the tympanostomy tube 30 has permitted the cutting edge distal ends 60, 62 to pierce and incise the tympanic membrane 98. In the position shown in FIG. 7, the distal legs 56, 58 are in their insertion position, and the distal ends 60, 62 just barely extend through the tympanic membrane 98, so that only the cutting edges 60, 62 have emerged into the tympanic cavity 102.

Turning now to FIG. 8, it will be noted that the plunger 84 is fully extended (to its permissible position) into the interior passageway 87 of the insertion tube 80, such that the distal end 112 of the plunger 84 is adjacent to the distal end 90 of the insertion tube 80. Note also that the distal facing surface of the plunger head 110 rests against the proximal end 88 of insertion tube 80. In this position, the radially outwardly extending flange 44 should rest against, or be close to resting against, the lateral surface 94 of the tympanic membrane 98. Additionally, the proximal portion 32 of the plunger 84 is positioned so that it is generally co-extensive with, and interiorly-disposed within the insertion tube 80.

The central portion, and the distal portion 34 of the tympanostomy tube 30 are disposed in the tympanic cavity, so that the laterally-facing surfaces 68, 70 (FIG. 3) of the distal legs 56, 58 are disposed adjacent to, and possibly resting against, the medially facing surface 100 of the tympanic membrane 98. It also should be noted that the distal legs 56, 58 have moved from their insertion position to their maintenance position. In the maintenance position, the first and second distal legs 56, 58 are disposed at an oblique angle to the axis of the central passageway 40, and preferably, are disposed generally perpendicularly to the axis of the central passageway 40.

Figure 10:
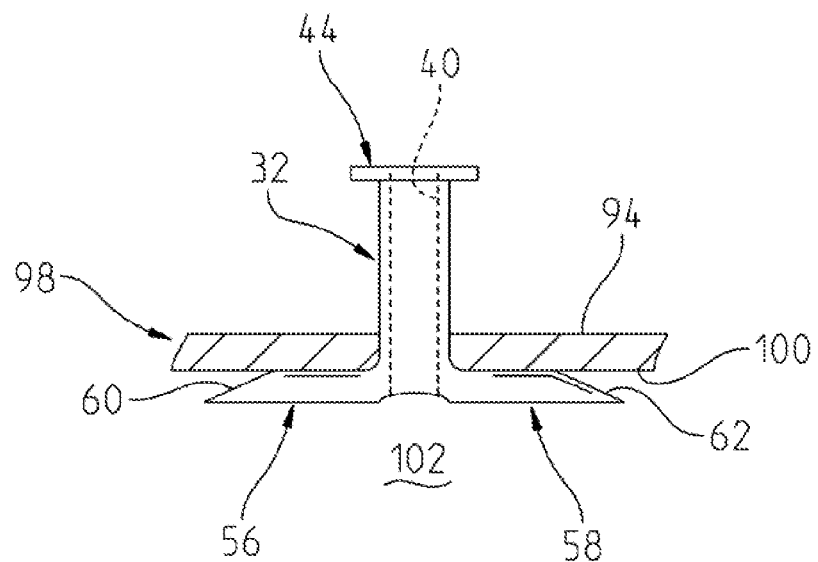
FIG. 10 is a sectional view showing the "T" type tympanostomy tube fully inserted in the tympanic membrane, with the tympanostomy tube in its maintenance position, and the insertion tube and plunger removed.

FIG. 9 is similar generally to FIG. 8. However, the plunger 84 is removed. As best shown in FIG. 10, the insertion tube 80 is also removed, and the final resting place of the tympanostomy tube 30 is shown, with the distal legs 56, 58 being moved into their maintenance position. It will be noted that because of the relatively enlarged radial diameter of the proximal end flange 44, and the relatively enlarged radial diameter of the legs 56, 58, the tympanostomy tube 30 (when in the maintenance position) is prevented from moving axially within the incision in the tympanic membrane 98. The flange 44 and the legs 56, 58 thereby help to prevent the tympanostomy tube 30 from being dislodged from the tympanic membrane 98, either by sliding laterally outwardly or medially inwardly. The axially extending passageway 40 provides a vent tube between the external auditory canal and the tympanic cavity 102, to help prevent the buildup of fluid therein.

An alternate grommet embodiment tympanostomy tube 200 is shown in FIGS. 11-20. The alternate embodiment tympanostomy tube 200 includes an enlarged diameter proximal end 202, an enlarged diameter distal end 204, and a reduced diameter central portion 206.

The central portion 206 is preferably generally cylindrical in configuration and is tubular in nature. The cylindrical reduced diameter central portion 206 includes a generally cylindrical outer wall 210 and a generally cylindrical inner wall 216. Cylindrical inner wall 216 defines an axially-extending passageway 218 that has a proximal opening 220 adjacent the proximal end 202 of the tube 200, and a distal opening 222 disposed adjacent to the distal end 204.

The axially-extending passageway 218 defines a long axis of the tympanostomy tube 200. The proximal and distal openings 220, 222 and passageway 18 all open so that air can flow between the outer ear, and in particular, the external auditory canal, and the middle ear, and in particular, the tympanic cavity 102. This flow of air helps to reduce the buildup of liquid mucus and fluid in the inner ear (tympanic cavity), and thus helps to combat infections and resultant ear aches.

Figure 11:
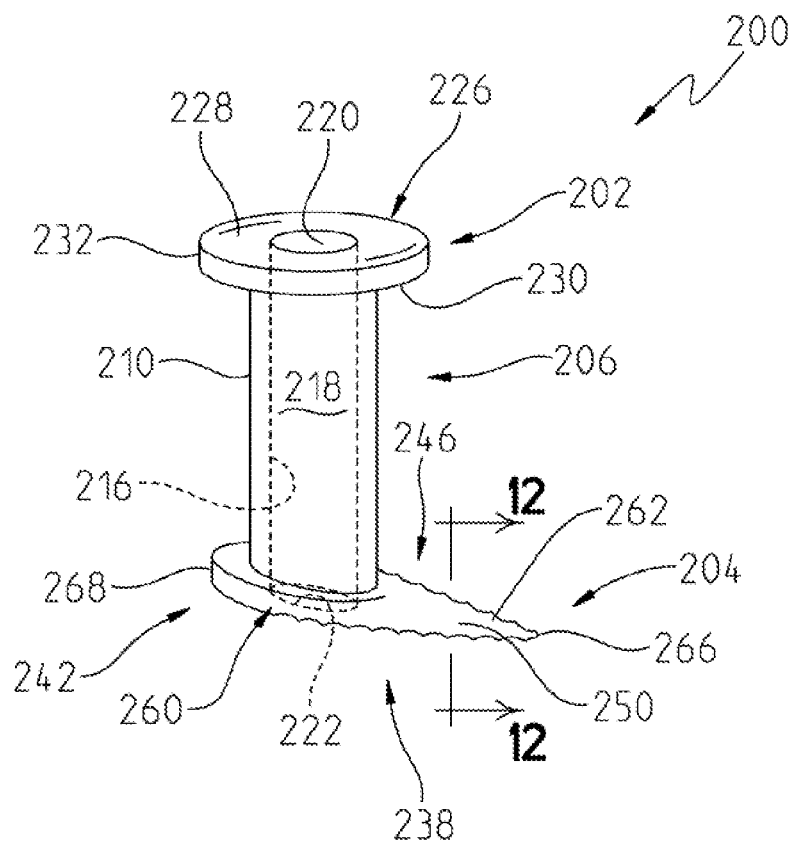
FIG. 11 is a perspective view of the first alternate embodiment "grommet" tympanostomy tube.
Figure 12:
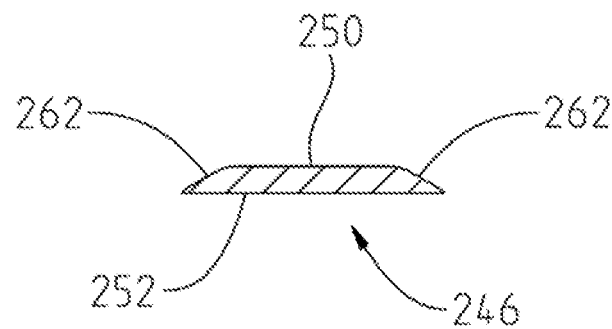
FIG. 12 is a sectional view taken along lines 12-12 of FIG. 11.
Figure 13:
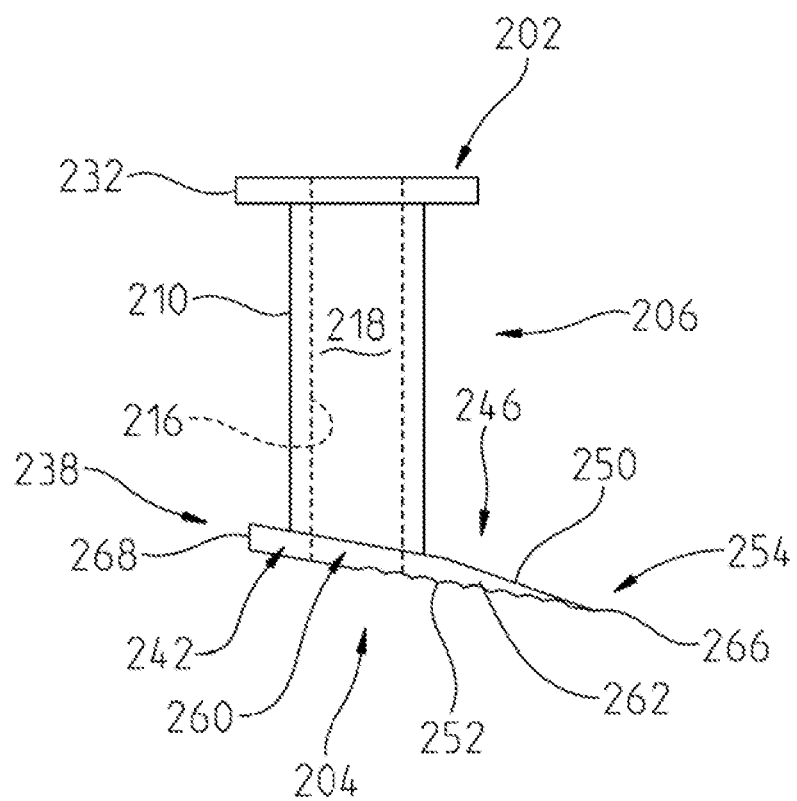
FIG. 13 is a side somewhat schematic view of the alternate embodiment tympanostomy tube shown in FIG. 11.
Figure 14:
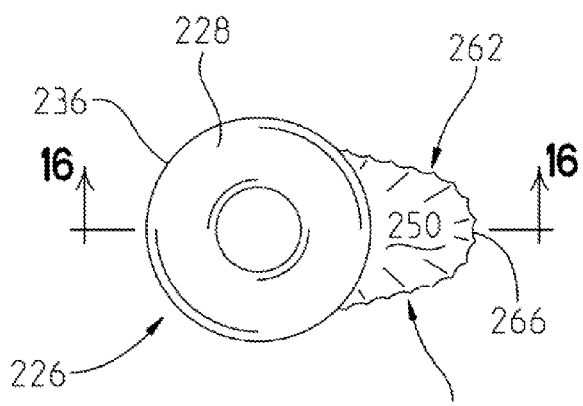
FIG. 14 is a top view of the tympanostomy tube shown in FIG. 11.

The proximal portion 202 includes a radially-extending flange 226 that includes a proximally-facing radially-extending surface 228, and an opposed, distally-facing radially-extending surface 230 (FIGS. 11, 14). The enlarged diameter radially-extending flange 226 performs a function similar to a nail head, as it helps to prevent the tympanostomy tube 200 from moving medially through the incision in which the tympanostomy tube 200 is placed. The radially-extending flange 226 also includes a radially outwardly-facing edge surface 232. Although the edge surface 232 is shown as being squared off, it can be a rounded-end surface 232 in the final device.

Figure 15:
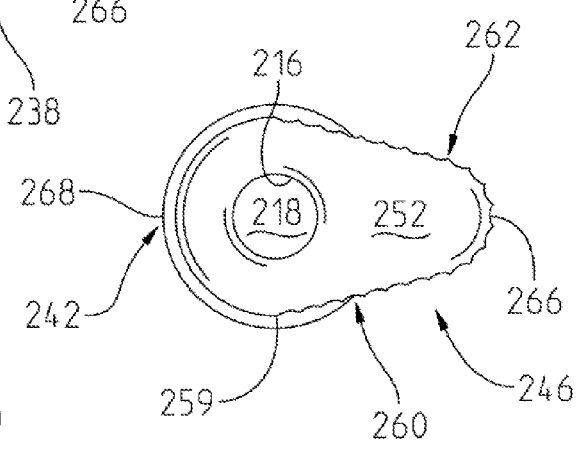
FIG. 15 is a bottom view of the tympanostomy tube grommet embodiment shown in FIG. 11.
Figure 16:
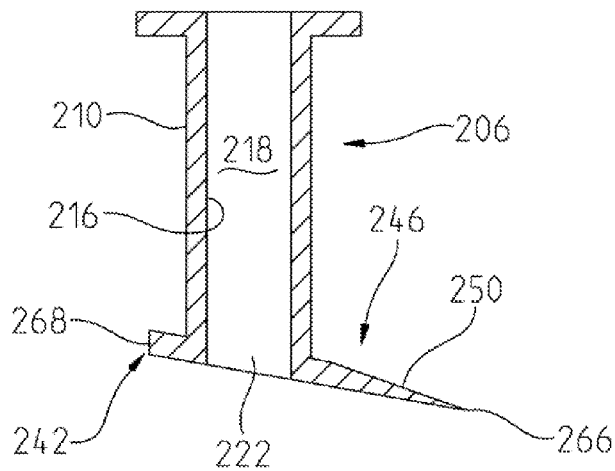
FIG. 16 is a sectional view taken along lines 16-16 of FIG. 14.

The distal portion 204 of the tympanostomy tube 202 includes an eccentric distal flange 238, that is generally ovaloid shaped in configuration. The eccentric distal flange 238 is placed in an eccentric relation relative to the axially-extending passageway 218, and central portion 206, so that the distal flange 238 includes a relatively shorter rear portion 242, and a relatively elongated forward incising portion 246 that includes an incising edge 262 of the tympanostomy tube 202 that cuts through the tympanic membrane 98, to form an incision in the tympanic membrane 98. The cutting (incising) edge 262 extends to the widest part of the ovoid distal forward incising portion 246 (FIGS. 11, 13A and 15). The tympanostomy tube 200 will simultaneously cut through and be passed through the incision to insert the tympanostomy tube 200 into the tympanic membrane 98 in one step.

It will also be noted that the tympanostomy tube's eccentric distal flange 238 is also placed at an oblique angle to the axis of the axially-extending passageway 218. Preferably, the eccentric distal flange 238 disposed at an angle up between about 110° and 150° relative to the long axis of the tympanostomy tube 200. This angled placement of the distal flange 238 helps to better position the tympanostomy tube 200 cutting edge 262 visually and ergonomically for incising and cutting through the tympanic membrane 98.

The eccentric distal flange 238 includes an upper proximally-facing surface 250, and a lower distally-facing surface 252. The distal flange 238 includes a perimetral surface 260 that includes a forward portion 246 having a cutting edge 262, and a non-cutting edge rearward portion 268. The thickness of a distal flange 238 varies in different areas of the flange 238. Preferably, the flange 238 is designed to be generally thinner in the forward portion 246, adjacent to the knife-shaped leading edge 266, and more relatively blunted and thicker at the trailing edge 268 of the smaller rear portion 242. Most preferably, the flange 238 is knife edge like, such that the distal flange 238 is thickest at the rearward edge 268, and is beveled, such that the thickness decreases as one moves forward to the forward portion 242, with the flange 238 being at its thinnest at forward leading edge 266.

The eccentric flange 238 should be made from material than can be designed to be sufficiently rigid, and sharp at the leading edge 266, and along the entire cutting edge 262 so as to be able to cut through the tympanic membrane 98. This toughness and sharpness can be achieved with either a plastic, composite or a metal distal edge flange 238. It should be noted that the cutting edge 262 may extend along the flange 238 edge 260 from the leading edge 266 to the widest point 259 (FIG. 15) of the flange 238 to ensure better cutting characteristics. Also, the edge 262 can be formed with micro-sized teeth or serrations to improve the cutting characteristics of the device and prevent ripping or rupturing the eardrum by puncture. It should further be noted that the leading edge 266 should be rounded, rather then pointed, so that the leading edge 266 performs a controlled cut rather than a pressure puncture, rupture or shred through the tympanic membrane 98.

Figure 17:
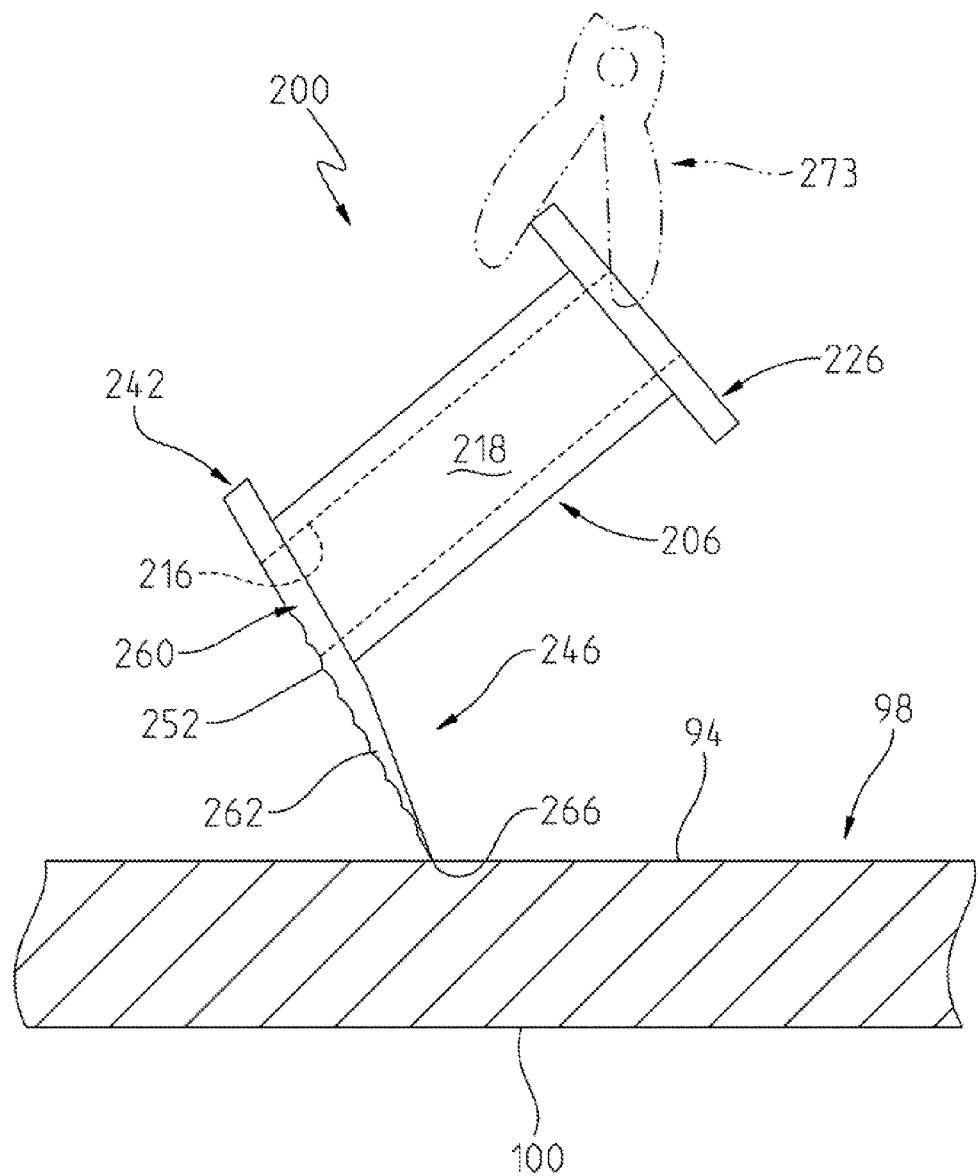
FIG. 17 is a side, partly schematic view of the grommet embodiment tympanostomy tube, showing said tube in a position where it is about to be inserted into a tympanic membrane.

The operation of the tympanostomy tube 200 will now be described with reference to FIGS. 17-20. Turning first to FIG. 17, the tube 200 is shown as being inserted in an ear canal (not shown). The proximal end 202 of the tube is gripped by forceps for so that the surgeon can manipulate the tympanostomy tube 200 into its appropriate position within the ear canal so that the distal flange 238 is placed adjacent to the lateral surface of the tympanic membrane 98. Preferably a thin forceps, such as an alligator type. Miltex micro ear forceps is employed wherein the first and second blades of the forceps are thin enough to enable the first blade to be inserted into passageway 218 to grip inner cylindrical surface 216, while the second blade is disposed exteriorly of the central portion to grip the exterior cylindrical surface 210. Through this gripping arrangement and forceps configuration, the surgeon can easily position the tube so that the long axis 218 of the tube 200 is disposed at an oblique angle, and preferably almost generally perpendicular to the plane of the laterally facing surface of the ear drum 98.

It will also be noted, that the cutting distal edge incising portion 266 is placed adjacent to the laterally-facing outer surface 94 of the tympanic membrane 98. The axis of the tube 200 (and its axially extending passageway) is held at an angle from perpendicular to the plane of the lateral surface of membrane 98, such that the axis of the axially-extending passageway 218 is disposed at an angle to the tympanic membrane 98 of approximately 45 degrees.

The forceps 273 are then manipulated by the surgeon to be moved in an axial, medial direction with micro-back-and-forth, knife-like cutting movements, toward the laterally outwardly facing surface 94 of the tympanic membrane 98, so that the leading edge 266 can cut into and cut through laterally outwardly-facing surface 94 the tympanic membrane 98. The remainder of the trailing cutting edge 262 follows and cuts its way through the incised opening of tympanic membrane 98. Preferably, the leading edge 266 of the incising edge 262 of the tube is designed to not "pierce" or "puncture" the tympanic membrane 87 since piercing or puncturing an ear drum 98 can lead to a fracture, shred or rupture of the eardrum 98. Eardrum damage that has occurred in prior art designs has caused the current preferred approach to comprise the "two-step" approach of using a knife to incise an opening into the eardrum followed by a secondary step of placing the tube in position.

Figure 18:
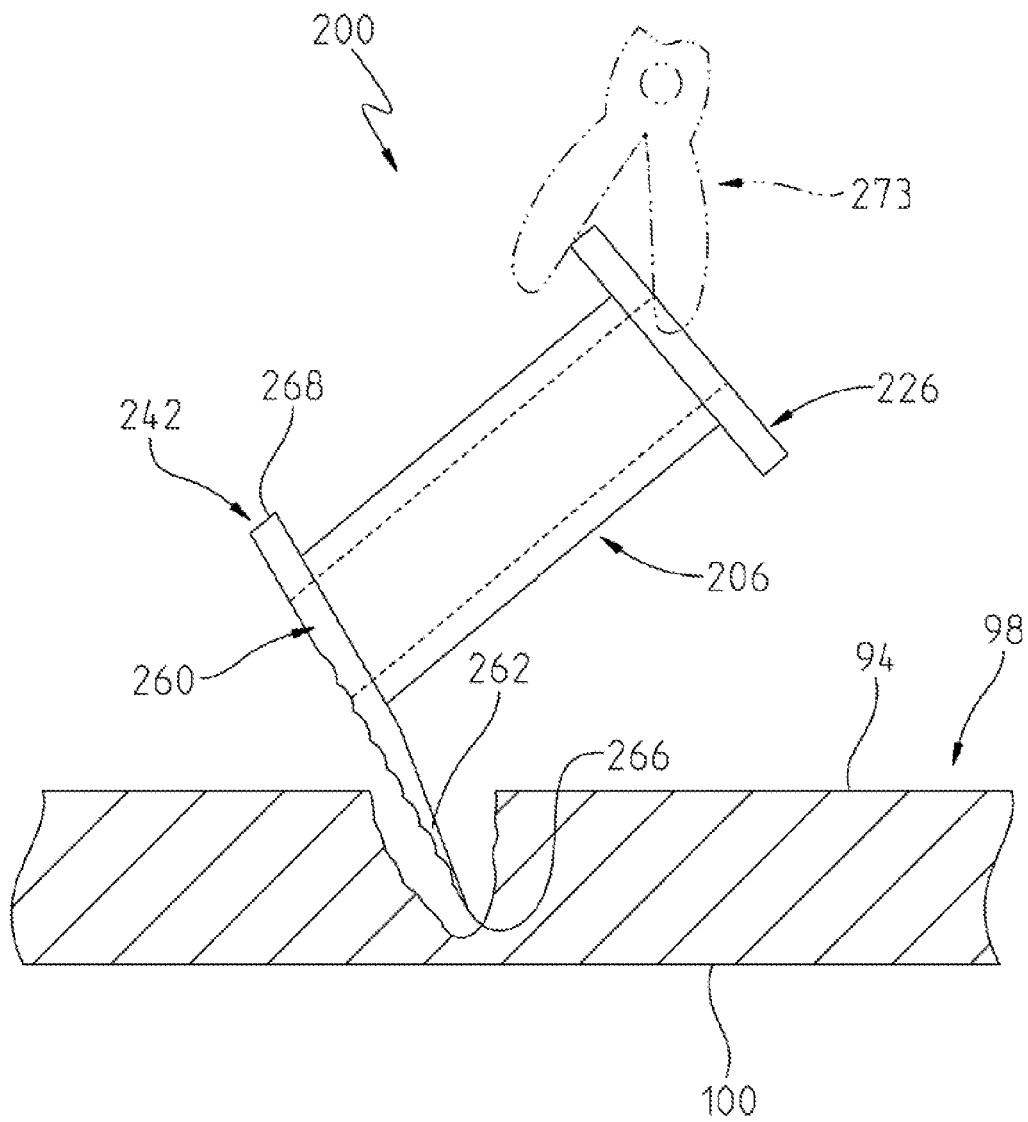
FIG. 18 is a side view, similar to FIG. 17, except that it shows the tympanostomy tube extending partially through the tympanic membrane.

The leading edge 266 generally provides the primary knife-like cutting surface, through the membrane 98. However, the entire cutting surface 262 also serves to cut the tympanic membrane in those areas of the tympanic membrane that are engaged by other areas of the cutting surface 262, as shown in FIG. 18.

Figure 19:
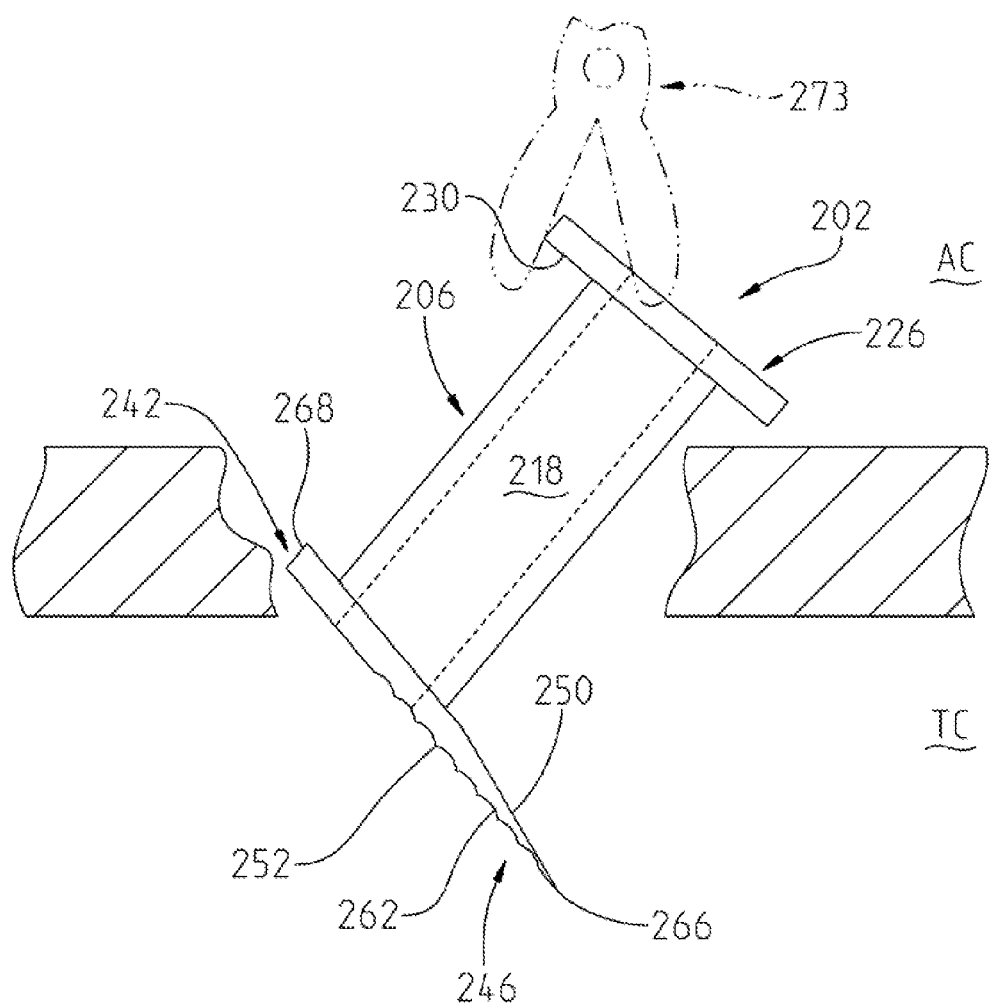
FIG. 19 is a progressive view, showing the tympanostomy tube being progressively inserted into the tympanic membrane.

Turning now to FIG. 19, the next progression shows that the forceps 273 have moved the tympanostomy tube 200 axially forwardly (and medially) to a point wherein the leading edge 266 has emerged into the tympanic cavity, TC where as the proximal edge 202 still resides in the external auditory canal, AC. Please note that the shown width of the incision is not indicative of a high volume of tympanic material being cut away. Rather, it is envisioned that the leading edge 266 will make a slit-like incision in the tympanic membrane 98 tissue, with the tissue being cut wide enough radially outwardly to allow the flange 238 to pass through the membrane 98, and then, to permit the tissue of the tympanic membrane 98 to engage the outer cylindrical surface 210 of the central portion 206 of the tympanostomy tube 200. As the incision heals, it will snugly engage the cylindrical surface 210 to help hold the tympanostomy tube 206 in its place in the tympanic membrane 98.

Figure 20:
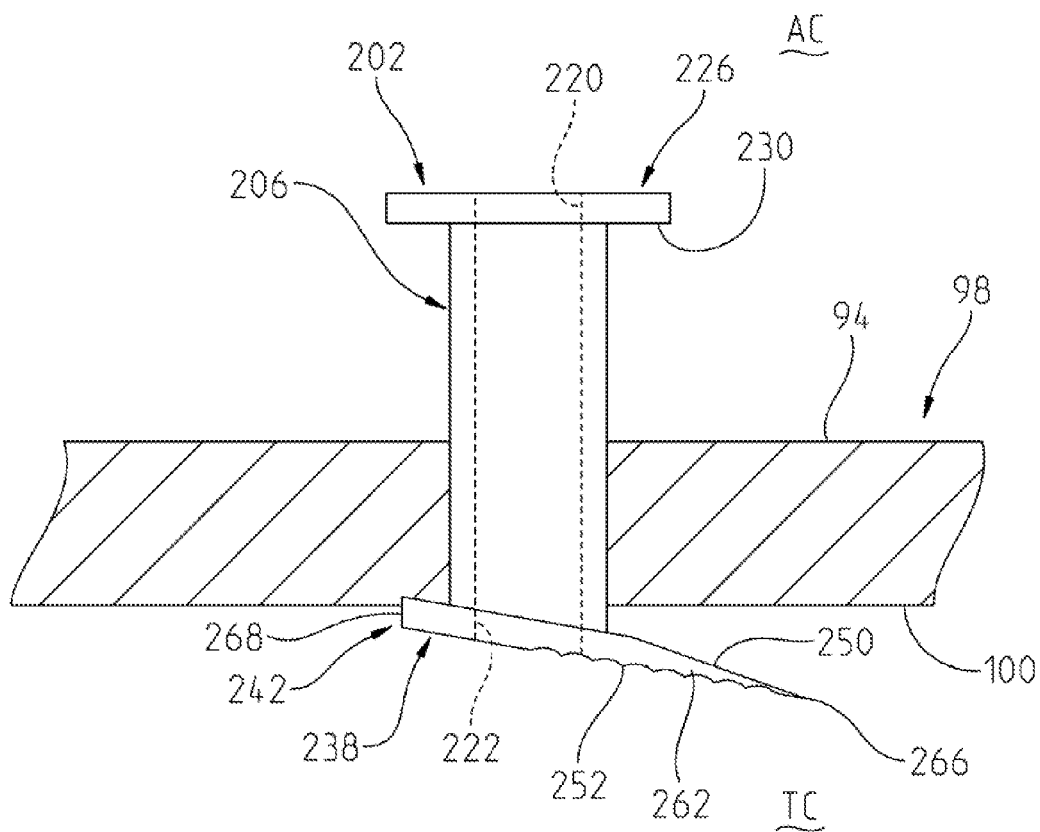
FIG. 20 is a side view, showing the grommet embodiment tympanostomy tube fully inserted into a tympanic membrane of the present invention.

Turning now to FIG. 20, the tympanostomy tube 200 is shown in its final position. It will be noted that the proximal portion 202 of the tympanostomy tube 200 is disposed within the external auditory canal. The proximal (first) flange 226, and in particular, the distal, medially-facing surface 230 of the proximal flange 226 rests against the lateral, outwardly-facing surface 94 of the tympanic membrane 98. As the diameter of the first flange 226 is generally greater than the diameter of the incision cut through the tympanic membrane 98, the width and diameter of the flange 226 will help to prevent the tympanostomy tube 200 from migrating in a medial direction into the tympanic cavity.

The distal flange 238 is inserted into the tympanic cavity 102. As the diameter of the distal second flange 238 is greater than the diameter of the incision, the distal flange 238 will help to prevent the tympanostomy tube 200 from migrating in a lateral direction out of the tympanic cavity TC, and into the external auditory canal AC. The proximal facing surface 250 engages and is placed against the medially-facing surface 100 of the tympanic membrane 98. Due to the oblique angle of the eccentric flange 238, the foreshortened rear portion 242 will more tightly and closely engage the medial surface 100 of the eardrum 98, than the more distally disposed forward leading edge portion 246.

Having described the invention in detail with referenced certain preferred embodiments, it will be appreciated that the scope and spirit of the invention incorporates modifications, variations and equivalents of the device described herein.

The invention claimed is:

1. A tympanostomy tube for insertion into and residence in a tympanic membrane of a mammal, the tympanostomy tube comprising:
    a body including a first end portion, a second end portion, a central portion disposed between the first and second end portions, and an axially extending passageway having a first open end disposed adjacent the first end portion, and a second open end disposed adjacent the second end portion, and an axis extending between the first open end and second open end,
    the first end portion including a relatively enlarged diameter, generally radially extending flange,
    the central portion including a reduced diameter portion sized for extending through and residing in tissue of the tympanic membrane,
    the second end portion including a relatively enlarged diameter second flange disposed adjacent the second end portion, the second flange including a perimetral edge having a sawing portion sufficiently sharp to saw through the tympanic membrane during insertion of the tympanostomy tube through the tympanic membrane, the sawing portion comprising a serrated edge containing sawing portion having a distal end being a rounded leading edge to increase the likelihood of the second flange forming an incision in the tympanic membrane and reducing the likelihood of the serrated edge containing sawing portion tearing or rupturing the tympanic membrane.

2. The tympanostomy tube of claim 1 wherein the second radially extending flange includes a relatively larger forwardly disposed portion, and a relatively smaller rear portion, wherein the forwardly disposed portion includes the serrated edge containing sawing portion, and the rounded leading edge.

3. The tympanostomy tube of claim 2 where the second flange has a tapered thickness, such that the rear portion is generally thicker than the forwardly disposed portion.

4. The tympanostomy tube of claim 1 wherein the second flange is disposed in a plane that is disposed at an oblique angle to the axis of the axially extending passageway.

5. The tympanostomy tube of claim 4 wherein the second flange is disposed at an oblique angle such that when the tympanostomy tube is placed against an exterior surface of a tympanic membrane such that the exterior surface is disposed in a plane generally perpendicular to the axis of the axially extending passageway, the serrated edge containing sawing portion of the forwardly disposed portion is disposed in a plane at an incising angle of less than about 90 degrees relative to the exterior surface of the tympanic membrane.

6. The tympanostomy tube of claim 5 where the incising angle of the serrated edge containing sawing portion of the forwardly disposed portion is between about 30 degrees and 70 degrees when the axis of the axially extending passageway is held generally perpendicular to an exterior surface of a tympanic membrane.

7. The tympanostomy tube of claim 1 wherein the second radially extending flange includes a relatively larger forwardly disposed portion, and a relatively smaller rear portion, and the second flange has a tapered thickness, such that the rear portion is generally thicker than serrated edge containing sawing portion of the forwardly disposed portion.

8. The tympanostomy tube of claim 1 wherein the second radially extending flange includes a forwardly disposed portion, and a rear portion, and the serrated edge containing sawing portion is disposed on the forwardly disposed portion.

9. The tympanostomy tube of claim 1 wherein the second flange is disposed in a plane that is disposed at an oblique angle to the axis of the axially extending passageway.

10. The tympanostomy tube of claim 1 wherein the second flange is disposed at an oblique angle to the axis of the axially extending passageway such that when the tympanostomy tube is placed against an exterior surface of a tympanic membrane such that the exterior surface is disposed in a plane generally perpendicular to the axis of the axially extending passageway, a sawing edge of the serrated edge containing sawing portion is disposed at an incising angle of less than about 90 degrees relative to the exterior surface of the tympanic membrane.

11. A tympanostomy tube for insertion into and residence in a tympanic membrane of a mammal, the tympanostomy tube comprising:
    a body including a first end portion, a second end portion, a central portion disposed between the first and second end portions, and an axially extending passageway having a first open end disposed adjacent the first end portion, and a second open end disposed adjacent the second end portion, and an axis extending between the first open end and second open end,
    the first end portion including a relatively enlarged diameter, generally radially extending flange,
    the central portion including a reduced diameter portion sized for extending through and residing in tissue of the tympanic membrane,
    the second end portion including a relatively enlarged diameter second flange disposed adjacent the second end portion, the second flange including a perimetral edge having a sawing portion sufficiently sharp to saw through the tympanic membrane during insertion of the tympanostomy tube through the tympanic membrane, the sawing portion comprising a serrated edge containing sawing portion having a distal end being a rounded leading edge configured for back and forth movement along the tympanic membrane to cause the serrated edge containing sawing portion to engage the tympanic membrane and to saw through the tympanic membrane to thereby increase the likelihood of the second flange cutting through the tympanic membrane and reducing the likelihood of the serrated edge containing sawing portion tearing or rupturing the tympanic membrane.

* * * * *